United States Patent [19]

Siddigi

[11] Patent Number: 4,532,107
[45] Date of Patent: Jul. 30, 1985

[54] REAGENT TEST DEVICE

[75] Inventor: M. Sultan Siddigi, Elkhart, Ind.

[73] Assignee: Miles Laboratories, Inc., Elkhart, Ind.

[21] Appl. No.: 593,535

[22] Filed: Mar. 26, 1984

[51] Int. Cl.³ .................... G01N 21/78; G01N 33/52
[52] U.S. Cl. ........................................ 422/56; 422/57
[58] Field of Search ............................ 422/56, 57, 58; 436/169, 170; 435/805

[56] References Cited

U.S. PATENT DOCUMENTS

| 3,802,842 | 4/1974 | Lange et al. ............... 422/57 X |
| 4,160,008 | 7/1979 | Fenocketti et al. .............. 422/56 |
| 4,250,256 | 2/1981 | Wielinger et al. ............. 422/58 X |
| 4,301,115 | 11/1981 | Rapkin et al. ..................... 422/56 |

FOREIGN PATENT DOCUMENTS

| 1852316 | 5/1962 | Fed. Rep. of Germany ........ 422/56 |
| 2655977 | 6/1978 | Fed. Rep. of Germany ........ 422/56 |
| 2739008 | 3/1979 | Fed. Rep. of Germany ........ 422/56 |
| WO82/02251 | 7/1982 | PCT Int'l Appl. ................... 422/56 |

Primary Examiner—Arnold Turk
Attorney, Agent, or Firm—Roger N. Coe

[57] ABSTRACT

The substrate of conventional reagent test devices is replaced by polyester screen material having a nominal filter rating of from about 80 to about 130 microns such that liquid present in the reagent matrix material of the test device is retained therein and prevented from running over onto other reagent matrix areas present on the same reagent test device.

8 Claims, No Drawings

REAGENT TEST DEVICE

FIELD OF THE INVENTION

The present invention relates to reagent test devices and, more particularly, reagent test devices employing a substrate material for reagent test devices which prevents or substantially eliminates runover problems responsible for cross contamination of reagents and interference with determinations or measurements based on colorimetric changes.

BACKGROUND OF THE INVENTION

The art of analytical chemistry has been greatly advanced since biochemistry began emerging as a primary scientific frontier, requiring increasingly sophisticated analytical methods and tools to solve problems. Likewise the medical profession has lent impetus to the growth of analytical chemistry, with its desiderata of both high precision and speed in obtaining results.

To satisfy the needs of the medical profession as well as other expanding technologies, such as the brewing industry, chemical manufacturing, etc., a myriad of analytical procedures, compositions and apparatus have evolved, including the so-called "dip-and-read" type reagent test device. Reagent test devices enjoy wide use in many analytical applications, especially in the chemical analysis of biological fluids, because of their relatively low cost, ease of usability, and speed in obtaining results. In medicine, for example, numerous physiological functions can be monitored merely by dipping a reagent strip test device into a sample of body fluid, such as urine or blood, and observing a detectable response, such as a change in color or a change in the amount of light reflected from or absorbed by the test device.

Many of the "dip-and-read" test devices for detecting body fluid components are capable of making quantitative or at least semiquantitative measurements. Thus, by measuring the response after a predetermined time, an analyst can obtain not only a positive indication of the presence of a particular constituent in a test sample, but also an estimate of how much of the constituent is present. Such test devices provide the physician with a facile diagnostic tool as well as the ability to gage the extent of disease or of bodily malfunction.

Illustrative of such test devices currently in use are products available from the Ames Division of Miles Laboratories, Inc. under the trademarks CLINISTIX, MULTISTIX, KETOSTIX, N-MULTISTIX, DIAS-TIX, DEXTROSTIX, and others. Test devices such as these usually comprise one or more carrier matrices, such as absorbent filter paper, having incorporated therein a particular reagent or reactant system which manifests a detectable response, e.g., a color change, in the presence of a specific test sample component or constituent. Depending on the reactant system incorporated with a particular matrix, these test devices can detect the presence of glucose, ketone bodies, bilirubin, urobilinogen, occult blood, nitrite, and other substances. A specific change in the intensity of color observed within a specific time range after contacting the test device with a sample is indicative of the presence of a particular constitutent and/or its concentration in the sample. Some of these test devices and their reagent systems are set forth in U.S. Pat. Nos. 3,123,443; 3,212,855; 3,814,668; etc.

Thus, it is customary for reagent test devices to contain more than one reagent bearing carrier matrix, in which each reagent bearing carrier matrix is capable of detecting a particular constituent in a liquid sample. For example, a reagent test device could contain a reagent bearing carrier matrix responsive to glucose in urine and another matrix responsive to ketones, such as acetoacetate, which is spaced from, but adjacent to, the glucose responsive matrix. Such a product is marketed by the Ames Division of Miles Laboratories, Inc. under the trademark KETO-DIASTIX. Another reagent test device marketed by the Ames Division of Miles Laboratories, Inc., N-MULTISTIX, contains eight adjacent reagent incorporated matrices providing analytical measurement of pH, protein, glucose, ketones, bilirubin, occult blood, nitrite, and urobilinogen.

Despite the obvious, time-proven advantages of such multiple reagent test devices, misuse can result in misinformation. These multiple analysis tools comprise complex chemical and catalytic systems, each reagent matrix containing a unique reactive system, responsive to its particular analyte. Thus, it is possible, if the reagent test device is misused, for chemicals to be transported by the liquid sample being analyzed from one carrier matrix on the reagent test device to another. Should this happen it is possible for reagents from one carrier matrix to interfer with those of another causing unreliable results. Although it is common in the reagent test device industry to provide detailed instructions on how this problem can be avoided, i.e., directions for properly manipulating a reagent test device by blotting excess fluid, etc., nevertheless ignorance or disregard of these instructions could permit reagents from one matrix to run over onto an adjacent one. It is the prevention of this "runover" problem that the present invention is primarily directed.

The elimination of runover has been long sought after and the present discovery, which is the cumulation of an extensive research effort, provides a very effective solution to this problem.

DISCUSSION OF THE PRIOR ART

The patent literature is replete with accounts of myriad attempts at curtailing runover, the great bulk of the emphasis being directed to two basic concepts: the adsorbance of runover liquid by bibulous layers placed beneath the reagent-bearing layers of reagent test devices; and the use of hydrophobic barriers between the spaced matrices. The former has met with moderate success, whereas the latter approach has not.

Of the multilayer type reagent test devices, U.S. Pat. No. 4,160,008 describes a test device in which the carrier matrices containing reagent formulations are provided with adsorbent underlayers which are separated therefrom by sample impervious barrier layers. Each matrix thus forms the upper layer of a laminate composite in which the barrier layer is disposed between the matrix and the adsorbent base layer, the composite being fixed to a suitable support such as a plastic substrate. When the test device is dipped into the liquid sample the portion of sample which would otherwise runover from one matrix to another is largely adsorbed into the underlayer of the latter through the exposed sides, the barrier layer of the composite segregating the adsorbent underlayer from the upper reagent layer.

U.S. Pat. No. 4,301,115 discloses and claims a test device comprising a base support member coated with a hydrophobic barrier layer to which a plurality of spaced apart reagent matrices are affixed. This approach virtually eliminates cross-contamination between adjacent reagent areas of multiple reagent test devices, but requires an extra step of applying hydrophobic material to the base support member of the reagent test device.

With respect to the development and use of barriers and/or barrier materials between reagent matrices, the patent art is replete with teachings, which in theory, at least, would minimize the runover problem.

U.S. Pat. No. 3,418,083 discloses an indicator-impregnated adsorbent carrier matrix treated with wax, oil or similar "hydrophobic" agents. It is stated that when a sample of blood is placed on the resulting reagent test device, only colorless liquid components permeate it, the proteinaceous, colored blood components remain on the surface where they can be removed. Thus, it is taught that the liquid portion bearing the analytes permeates the reagent matrix pad and color interference is precluded.

Still another prior art patent, U.S. Pat. No. 3,001,915, describes an adsorbent paper reagent test device having spaced reagent-impregnated test areas for more than one sample component, each such area being separated from the other reagent-impregnated test area by a nonadsorbent barrier portion. The barrier is provided by impregnation with materials such as polystyrene, rosin, paraffin and various cellulose esters. The reagent strip is prepared, according to the reference, by impregnating a portion of a paper pad with a glucose sensitive reagent system. When the reagent strip is dry, a solution of one or more of the barrier materials is applied to the paper adjacent the glucose sensitive reagent material. After further drying a protein sensitive reagent system is applied and the process is repeated with alternate applications of reagent and barrier solutions, with drying steps inbetween.

Yet an earlier patent, U.S. Pat. No. 2,129,754, describes the impregnation of filter paper with paraffin wax whereby specific areas are left unimpregnated and these areas are treated with indicator systems for a particular analyte.

In U.S. Pat. No. 3,006,735 the concept of barrier material impregnated between reagent areas of a reagent test device is carried one step further by providing successive reagent areas responsive to different degrees of water hardness. Water repellent material, such as oils, waxes, silicones, and printer's varnish, is impregnated between these reagent test areas. Like the proceeding two patents this citation is restricted to paper or like bibulous material wherein reagent and barrier material alike are impregnated sequentially along its length.

Similarly, U.S. Pat. Nos. 3,011,874 and 3,127,281 teach the use of hydrophobic barrier materials impregnated in part of a reagent test device in order to separate one reagent area from another and thereby avoid contamination.

Yet another patent which mentions the separation of indicator reagent sites by the use of nonadsorbent or hydrophobic materials is U.S. Pat. No. 3,964,871.

Whereas the foregoing patents represent what is believed to be the most pertinent prior art to the present invention, it should be noted that currently marketed reagent test device products for the most part contain reagent impregnated matrices affixed to hydrophobic organoplastic material. Thus, the multiple reagent test device known as N-MULTISTIX contains eight different reagent impregnated matrices mounted on polystyrene film. Since polystyrene is hydrophobic, the reagent strip can be said to have hydrophobic interstices between adjacent matrices.

Despite lip service given by prior art accounts to eliminating runover, the fact remains that the problem continues to exist. The approaches disclosed in U.S. Pat. Nos. 4,160,008 and 4,301,115 have come the closest to eliminating this runover problem.

Prior art attempts using wax, oils, silicones, etc., have not curtailed runover to a clinically significant extent; and what modest advances have been made are more than offset by serious drawbacks inherent to such attempts. For example, applying hydrophobic material only at reagent area interstices embodies enormous technical problems, especially when compared with the current technics for manufacturing dip-and-read reagent test devices. Besides the obvious extra steps required by interstitial application, there is the danger of some of the hydrophobic material overlapping the reagent area thereby interfering with the paramount purpose of the reagent test device. Moreover, none of the prior art substances provides a suitable surface for adhesion.

Even if the above shortcomings were not prohibitive enough, the prior art hydrophobic substances lack a degree of hydrophobicity required to prevent runover. They do not provide a sufficient contact angle to achieve the required hydrophobicity, nor do they provide a suitable surface for binding either the adsorbent matrices or the reagent, where reagent is coated directly on the substrate surface.

The present invention virtually eliminates cross-contamination between adjacent reagent areas of multiple reagent test device matrices. Success in eliminating runover problems, which causes cross-contamination and results in false determinations, is achieved by replacing the conventional substrate, e.g., Trycite (polystyrene) with a polyester screen. Unlike Trycite, the polyester screen substantially eliminates migration of liquid from one reagent matrix to another. Significantly, no change in the conventional manufacturing procedures is required for forming the improved reagent test devices.

SUMMARY OF THE INVENTION

An object of the present invention is to replace conventional reagent test device supporting substrate with a polyester screen material which prevents or substantially eliminates runover problems on reagent test devices containing multiple carrier matrices.

Still another object of the present invention is to provide an inexpensive and effective means for eliminating or materially reducing runover.

In accordance with the present invention, a hydrophilic polyester screen twill weave material having a nominal filter rating of from about 80 to about 130 microns and preferably from about 80 to about 90 microns is employed instead of hydrophobic Trycite as substrate material to which reagent matrices are attached by means of a double backed adhesive material in the conventional manner to provide a configuration substantially identical to that of present reagent test devices.

DESCRIPTION OF THE PREFERRED EMBODIMENTS

In accordance with the present invention, reagent test devices are prepared in the conventional manner with the exception that the Trycite substrate conventionally used is replaced with a hydrophilic polyester screen twill weave material having nominal filter rating from 80 to about 130 microns and preferably from about 80 to about 90 microns.

The preferred hydrophilic polyester screen twill weave material is polyethylene terephthalate formed into twilled cloth woven with a greater number of threads in the warp direction than in the weft direction, usually all the same diameter. In both directions, the threads pass over three and under one thread, in a progressive step pattern. Less preferred as a screen weave is the twill square weave in which each weft thread typically passes over two warp threads and under one, producing square openings in a diagonal pattern.

Particularly preferred is polyester fiber PE1020K-86 manufactured by Tetko Inc. of Elmsford, N.Y., U.S.A. This polyester fiber has a specific gravity of 1.36, a melting point (both wet and dry) of 15 to 30. The resulting twill filter fabric has a nominal filter rating of 86 microns, and a mesh count per inch of 165 (warp)/38 (weft).

In addition to its other attributes, the polyester screen material contemplated by the present invention is low in cost, has easy handling characteristics, is resistant to chemical attack and has good stability.

The reagent ribbon or matrix material applied to the polyester screen can be formed from any suitable material. U.S. Pat. No. 3,846,247 teaches the use of felt, porous ceramic material and woven or matted glass fibers. Additionally, U.S. Pat. No. 3,552,928 teaches the use of wood material, cloth, sponge material and argillaceous substances. The use of synthetic resin fleeces and glass fiber felts as carrier matrix is suggested in British Pat. No. 1,369,139. Another British Pat. No. 1,349,623, proposed the use of light permeable meshwork of thin filaments as a cover for an underlying paper matrix. Polyimide fibers are taught in French Pat. No. 2,170,397. Notwithstanding these suggestions, however, the material predominantly used in the art as a carrier matrix and that which is especially useful in the present invention is bibulous paper, such as filter paper.

The reagent ribbon or matrix material normally contains reagent(s) prior to its attachment to the substrate by suitable means, e.g., double faced adhesive tape such as Double Stick available from the 3M Company. Following conventional techniques, a card of substrate material containing reagent ribbons adhesively bound thereto is cut width wise to form reagent test devices measuring 8 by 0.5 centimeters, having 0.5 centimenter square carrier matrices at one end thereof with the other end of the substrate serving as a handle for the reagent test device.

The following examples illustrate the effectiveness of the invention, comparing test devices made in accordance with the invention with conventional and other test devices. Reagent test matrices for determining urobilinogen and nitrite were used in the examples since these matrices have traditionally resulted in the worst runover problem for reagent test devices.

EXAMPLE I

To demonstrate the effectiveness of the present invention reagent strips were formed for control purposes using conventional Trycite substrate to which alternate reagent matrix areas were attached in conventional fashion using double backed 3M tape. The alternate reagent matrix areas comprised filter paper impregnated with reagents specific for the detection of urobilinogen and nitrite, respectively. These two tests have traditionally resulted in the worst runover problem for test devices.

The test means for urobilinogen were prepared in accordance with Examples I and II of U.S. Pat. No. 4,158,546.

The composition sensitive to nitrite was prepared from the following ingredients: Gantrex AN139 (5 g), methanol (250 ml), p-arsanilic acid (1.3 g) and sodium lauryl sulfate (2.5 g). These ingredients were dissolved, in the order shown, in 250 ml of distilled water with care being taken to insure that each ingredient was completely dissolved before adding the next ingredient. Upon completion, the solution was hazy and colorless. Test means were prepared, in a fashion similar to that for the urobilinogen test means, by impregnating filter paper with the resulting solution.

A gap of 0.08 inches was present between the alternating urobilinogen-nitrite test means present on the resulting control test device. Altogether, each test device had four urobilinogen test means and four nitrite test means.

For purposes of preparing test devices in accordance with the present invention Tetko polyethylene terephthalate twill screen (PE1020K-86), having a nominal filter rating of 86 microns, was used in place of Trycite and urobilinogen and nitrite test means, identical to those described above for the control test device, were applied to the polyester screen material.

The resulting control test devices and polyester screen test devices were each dipped in urine, held flat and observed after three minutes for runover or other evidence of cross-contamination. The control devices exhibited 55 percent runover whereas test devices prepared in accordance with the present invention demonstrated 0 percent runover.

EXAMPLE II

The procedure of Example I was again followed to make screen fabric reagent test devices except that polyethylene terephthalate twill screen weave having a nominal filter rating of 120 microns (Tetko PE1005K-120) was employed as the screen fabric. The runover was determined to be almost nonexistent, amounting to only 0.02 percent.

EXAMPLE III

When Example I was repeated using polyethylene terephthalate (polyester) twill screen weave having a nominal filter rating of 55 microns (Tetko PE1051K-55) the runover was 60 percent.

EXAMPLE IV

When Example I was run using a polypropylene twill screen weave, having a nominal filter rating of 36 microns (Tetko PP1050K-36), for the polyester screen, the runover amounted to 50 percent.

From the foregoing, it will be seen that this invention is well adapted to attain all of the ends and objects hereinabove set forth, together with other advantages which are obvious and which are inherent to the system. The present invention has the advantages of convenience, simplicity, relatively inexpensiveness, positiveness, effectiveness, durability, accuracy and directness of action. The invention substantially overcomes problems associated with runover which have been a continuing and long felt problem with multiple reagent test devices. The invention provides a very effective, simple and inexpensive way of eliminating or materially reducing the runover problem. Test devices prepared in accordance with the present invention eliminate the "bridging" of liquid between test matrices on test device and hence the migration of liquid from one test matrix to another. In addition, the present invention can effectively be utilized in conjunction with conventional techniques, or methods for forming reagent test devices. There is no extra layer which must be applied to reagent test devices in order to control the runover problem. If desired the present invention can even be used in conjunction with other techniques found useful to control the runover problem. Thus, the present invention could be utilized in conjunction with techniques in the prior art which rely on the use of hydrophobic barrier layers affixed to reagent test devices.

Obviously, many other modifications and variations of the invention as hereinbefore set forth can be made without departing from the spirit and scope thereof.

What is claimed is:

1. Reagent test device comprising multiple reagent carrier matrices attached in spaced relationship to one side of a supporting substrate, wherein the substrate is a hydrophilic polyester screen material having a nominal filter rating of from about 80 to about 130 microns.

2. The test device of claim 1 in which the nominal filter rating is from about 80 to about 90 microns.

3. The test device of claim 1 in which the carrier matrices comprise filter paper.

4. The test device of claim 3 in which the substrate is polyethylene terephthalate.

5. The test device of claim 4 in which the substrate has a nominal filter rating of 86 microns.

6. The test device of claim 3 in which the screen material is a twill weave.

7. The test device of claim 4 in which the screen material is a twill weave.

8. A colorimetric reagent test device comprising multiple reagent carrier matrices incorporated with a colorimetric reagent or reactant system attached in spaced relationship to one side of a supporting substrate, wherein the supporting substrate is a hydrophilic polyester screen material having a nominal filter rating of from about 80 to about 130 microns.

* * * * *